(12) United States Patent
Crich et al.

(10) Patent No.: US 6,620,972 B2
(45) Date of Patent: Sep. 16, 2003

(54) METHOD OF OXIDIZING AN ALCOHOL USING A RECYCLABLE FLUOROUS SULFOXIDE

(75) Inventors: David Crich, Chicago, IL (US); Santhosh Neelamkavil, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 10/174,269

(22) Filed: Jun. 18, 2002

(65) Prior Publication Data

US 2003/0105363 A1 Jun. 5, 2003

Related U.S. Application Data

(60) Provisional application No. 60/301,568, filed on Jun. 28, 2001.

(51) Int. Cl.[7] .................. C07C 317/00; C07C 47/00; C07C 49/587
(52) U.S. Cl. .................. 568/27; 568/420; 568/303
(58) Field of Search .................. 568/27, 420, 425, 568/303, 322

(56) References Cited

U.S. PATENT DOCUMENTS 3,290,380 A * 12/1966 Aichenegg et al. ........... 568/27
3,660,496 A *  5/1972 Schmerling .................. 568/27

FOREIGN PATENT DOCUMENTS

FR            2516920           5/1983

OTHER PUBLICATIONS

CA:137:262826 abs of Tetrahedron by Rocaboy et al 58(20) pp 4007–4014 2002.*
Chemical abstracts vol. 47 No. 10478 (a) Nov. 1953.*
CA:128:127596 abs of Russian Journal of Organic Chemistry by Timoshenko 33(1) pp 60–65 1997.*
CA:131:129566 abs of Russian Journal of Organic Chemistry by Shermolovich et al 34(8) pp 1112–1116 1998.*
CA:131:180265 abs of WO9942109 Aug. 1999.*
Crich et al., *J. Am. Chem. Soc.*, *123*, pp. 7449–7450 (2001).
I. E. Marko et al., *J. Am. Chem. Soc.*, *119*, pp. 12661–12662 (1997).
I. E. Marko et al., *J. Org. Chem.*, *63*, pp. 7576–7577 (1998).
I. E. Marko et al., *J. Org. Chem.*, *64*, pp. 2433–2439 (1999).
T. T. Tidwell, *Org. React.*, *39*, pp. 297–572 (1990).
T. T. Tidwell, *Synthesis*, pp. 857–870 (1990).
A. J. Mancuso et al., *Synthesis*, pp. 165–185 (1981).
A. Studer et al., *Science*, *275*, pp. 823–826 (1997).
I. T. Horvath, *Acc. Chem. Res.*, *31*, pp. 641–650 (1998).
D. P. Curran, *Angew. Chem. Int. Ed. Engl.*, *37*, pp. 1174–1196 (1998).
Q. Zhang et al., *J. Org. Chem.*, *65*, pp. 8866–8873 (2000).
J. Drabowicz et al., *Synth. Commun.*, *11*, pp. 1025–1030 (1981).
Y. Liu et al., *J. Org. Chem.*, *61*, pp. 7856–7859 (1996).
J. M. Harris et al., *J. Org. Chem.*, *63*, pp. 2407–2409 (1998).
S. Dieng et al., *J. Fluorine Chem.*, *28*, pp. 425–440 (1985).
A. Ogawa et al., *J. Org. Chem.*, *62*, pp. 450–451 (1997).

* cited by examiner

*Primary Examiner*—Jean F. Vollano
(74) *Attorney, Agent, or Firm*—Marshall, Gerstein & Borun

(57) ABSTRACT

A method of oxidizing primary and secondary alcohols to an aldehyde or ketone using a fluorous sulfoxide or a fluorous sulfide is disclosed. The method includes regenerating and recycling the fluorous sulfoxide.

19 Claims, No Drawings

METHOD OF OXIDIZING AN ALCOHOL USING A RECYCLABLE FLUOROUS SULFOXIDE

CROSS REFERENCE TO RELATED APPLICATION

This application claims the benefit of U.S. provisional patent application No. 60/301,568, filed Jun. 28, 2001.

This invention was made with government support under CHE 9986200 awarded by the National Science Foundation.

FIELD OF THE INVENTION

The present invention relates to fluorinated sulfoxides and to a facile and environmentally acceptable method of oxidizing primary and secondary alcohols to aldehydes and ketones, respectively. More particularly, the invention relates to the oxidation of alcohols using a recyclable, fluorous sulfoxide.

BACKGROUND OF THE INVENTION

The controlled oxidation of primary and secondary alcohols to aldehydes and ketones, respectively, is one of the most common transformations in organic chemistry. It is not surprising, therefore, that methods of performing such oxidations are consistently being refined and improved. Major advances in recent years include use of a catalytic tetrapropylammonium perruthenate oxidant and the use of 2-iodoxybenzoic acid.

A wide variety of other reagents are utilized in the oxidation of primary and secondary alcohols. However, many of these reagents are metal based and, because of toxicity and environmental concerns, are becoming increasingly unsuitable for use in industrial applications. This is especially the case in the manufacture of fine chemicals and pharmaceuticals wherein, aside from the usual problems of waste disposal, even trace amounts of toxic transition metal salts in the reaction product are unacceptable. The high level of interest in environmentally friendly oxidations is illustrated by the recent number of publications directed to transition metal catalyzed processes with molecular oxygen.

One of the more popular alcohol oxidation methods is the Swern oxidation, which employs a combination of dimethyl sulfoxide, oxalyl chloride, and an organic base. In particular, the Swern oxidation is widely used in the manufacture of fine chemicals, especially pharmaceuticals, because the reaction is metal free and relatively inexpensive. However, a stoichiometric by-product of the Swern oxidation is dimethyl sulfide, which is an extremely volatile (b.p. 37° C.) and foul-smelling compound. The generation of dimethyl sulfide also is environmentally unacceptable, which makes the Swern reaction undesirable for large commercial applications. For example, if used in a large reaction scale, the Swern oxidation process would require scrubbing of the waste stream.

Modification of the Swern oxidation to eliminate the formation of dimethyl sulfide has been addressed by using polymer-supported and extractable nonvolatile reagents. See J. M. Harris et al., *J. Org. Chem.*, 63, p. 2407 (1998), and Y. Liu et al., *J. Org. Chem.*, 61, p. 7856 (1996). Each of these modifications suffers from disadvantages. In particular, in the base soluble sulfoxide method, a competing Pummerer reaction that occurs during the course of the oxidation makes recycling inefficient. The polymer-supported analogs are less than ideal on a large scale because of the considerable bulk of polymer required, and because of the obvious difficulty in monitoring a reoxidation process during recycling. Transition metal catalyzed oxidations using molecular oxygen, while having potential in the large scale oxidations of simple industrial alcohols, are not considered suitable for the oxidation of highly functionalized and sensitive alcohols prepared in the modern pharmaceutical industry.

The present invention is directed to an improved method of oxidizing primary and secondary alcohols, in a large scale, that overcomes the disadvantages associated with prior oxidation methods.

SUMMARY OF THE INVENTION

The commercial, environmentally friendly preparation of aldehydes and ketones by oxidation of a primary or secondary alcohol, respectively, has been hindered because of the use of metal-based reactions or the generation of noxious by-products, such as dimethyl sulfide. Therefore, the present invention is directed to a commercial scale method of synthesizing aldehydes and ketones that overcome the environmental and disposal problems associated with prior oxidation methods.

In particular, the present invention is directed to a method of preparing aldehydes and ketones from a primary or secondary alcohol, respectively, using a modification of the Swern reaction. In particular, the Swern reaction is modified by using a fluorous sulfoxide to overcome problems associated with the use of dimethyl sulfoxide in a standard Swern reaction.

The Swern reaction was investigated for modification because of the popularity of the reaction with respect to preparing aldehydes and ketones. An important feature of the investigation was to avoid the generation of environmentally unfriendly dimethyl sulfide.

Accordingly, the present invention is directed to a modified Swern reaction wherein a fluorous sulfoxide is substituted for the dimethyl sulfoxide Swern reagent. In particular, one aspect of the present invention is to provide a fluorous Swern reagent that overcomes the disadvantages associated with dimethyl sulfoxide. The fluorous Swern reagent has a general structural formula (I)

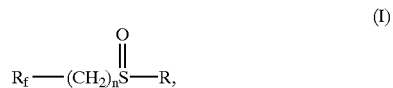

(I)

wherein $R_f$ is a fluorinated hydrocarbon chain containing one to twelve carbon atoms; R is $C_{1-4}$alkyl or $(CH_2)_n$—$R_f$; and n is an integer 1 to 3.

Another aspect of the present invention is to provide a fluorous Swern reagent of structural formula (I) wherein $R_f$ contains four to ten carbon atoms and, preferably, is perfluorinated; R is $C_{1-4}$alkyl, preferably, methyl or ethyl; and n is 2.

Another aspect of the present invention is to provide a fluorous Swern reagent that avoids the stoichiometric generation of environmentally unfriendly dimethyl sulfide, incorporates a single, relatively short perfluoroalkyl chain (i.e., four to eight carbon atoms) soluble in fluorinated solvents, and is economical and easy to synthesize.

Yet another aspect of the present invention is to provide a method of preparing an aldehyde or a ketone from a primary or secondary alcohol, respectively, using a fluorous sulfoxide of structural formula (I).

Still another aspect of the present invention is to provide a method of recycling the fluorous sulfoxide of structural formula (I) by separateing and oxidizing a fluorous sulfide generated in the Swern reaction to regenerate the fluorous sulfoxide of structural formula (I).

These and other novel aspect and advantages of the present invention will become apparent from the following detailed description of the preferred embodiments.

DETAILED DESCRIPTION OF THE PREFERRED EMBODIMENTS

The present invention is directed to a modified Swern reaction for the facile commercial preparation of aldehydes and ketones from a primary or secondary alcohol, respectively. The modified Swern reaction utilizes a fluorous sulfoxide that overcomes the problems associated with dimethyl sulfoxide utilized in a standard Swern reaction.

The present invention, therefore, is directed to fluorous sulfoxides useful in a Swern reaction, and readily recycled by continuous extraction and oxidation steps. Using a virgin or a recycled fluorous sulfoxide of structural formula (I) retains all the desirable properties of the classic Swern reaction, while overcoming the problems associated with the classic Swern reaction.

The fluorous sulfoxides useful in the present invention have a structural formula (I)

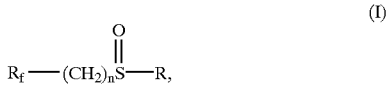

(I)

wherein $R_f$ is a fluorinated hydrocarbon chain having one to twelve carbon atoms; R is $C_{1-4}$alkyl or $(CH_2)_n$—$R_f$; and n is an integer 1 to 3.

An important feature of the fluorous sulfoxide (I), and the present Swern oxidation method, is recycability of the fluorous sulfoxide. The recycling process includes an extraction step using a perfluorinated hydrocarbon solvent and an oxidation step using hydrogen peroxide. Therefore, fluorous sulfoxides (I) require a sufficient amount of fluorine for solubilization in a perfluorinated solvent. It has been found that a fluorous sulfoxide requires at least 35% fluorine by weight, and preferably at least about 38% fluorine, by weight. In general, the fluorous sulfoxide contains at least 35% to about 65%, and preferably about 38% to about 60%, by weight, fluorine. To achieve the full advantage of the present invention, the fluorous sulfoxide contains about 40% to about 60%, by weight, fluorine.

The weight percent fluorine in the fluorous sulfoxide is determined by the length of the $R_f$ chain or chains, and the amount of fluorine in the $R_f$ chain or chains. If the fluorous sulfoxide contains two $R_f$ groups, the $R_f$ groups can be the same or different.

An important feature of a fluorous sulfoxide of the present invention is the length of the spacer linking the fluorinated alkyl chain to the S→O moiety of the sulfoxide. Reagents lacking a spacer, i.e., having a fluorinated alkyl chain bound directly to the S→O moiety (i.e., n=0), are unsuitable because the nucleophilicity of the fluorous sulfoxide is reduced, and, therefore, have a disadvantage of reduced activity. A linker having one methylene group (i.e., n=1) is useful, but has a disadvantage of eliminating hydrogen fluoride (HF) from the sulfoxide. A linker having three methylene groups also is effective, but requires a longer $R_f$ chain for efficient extraction in the recycling process. Therefore, fluorous sulfoxides (I) having two methylene group spacers (i.e., n=2) are preferred, and an especially preferred embodiment utilizes perfluorinated $R_f$ chains, e.g., perfluorohexyl, as the fluorinated alkyl chain. A perfluorohexyl group provides a flourous Swern reagent having 60.2%, by weight, fluorine, when R is methyl.

Preferred fluorous sulfoxides (I) for use in the modified Swern reaction, therefore, contain one $R_f$ group containing four to ten, and more preferably six to eight, carbon atoms. The $R_f$ group preferably is perfluorinated. In preferred embodiments, the R group is methyl or ethyl, and n is 2.

Important features of the present invention included (a) the facile preparation of crystalline, odor-free sulfoxides (e.g., 3,3,4,4,5,5,6,6,6-nonafluorohexyl methyl sulfoxide, hereafter termed "fluorous DMSO," and its higher and lower homologs), (b) their use in Swern oxidation reactions, and (c) their recycling using a biphasic extraction with an industrial perfluorinated hydrocarbon solvent and reoxidation using hydrogen peroxide. Fluorous sulfides (S. Dieng et al., *J. Fluorine Chem.*, 28, pp. 425–440 (1985)) and sulfoxides similar to fluorous DMSO have been synthesized previously using alternative, longer routes. However, their use in a Swern oxidation has not been disclosed. Benzotrifluoride has been described as a fluorinated solvent in standard Swern reactions, using DMSO, on fluorous substrates (A. Ogawan et al., *J. Org. Chem.*, 62, pp. 450–451 (1997)).

Fluorous DMSO was synthesized by (a) a sodium borohydride reduction of dimethyl disulfide, followed by (b) a nucleophilic displacement of iodine from commercial 3,3,4,4,5,5,6,6,6-nonafluoro-hexyl iodide, and (c) a subsequent oxidation with hydrogen peroxide (J. Drabowicz et al., *Synth. Commun.*, 66, pp. 1025–1030 (1981)). Fluorous DMSO is an odorless, white crystalline compound. Overoxidation to the sulfone was not observed in step (c) when using inexpensive hydrogen peroxide as the oxidizing agent.

Fluorous DMSO can be activated with oxalyl chloride, for example, in dichloromethane ($CH_2Cl_2$) at $-30°$ C., subsequently treated with the substrate (i.e., a primary or secondary alcohol), then a base, e.g., diisopropylethylamine, which essentially is the standard Swern oxidation. The practicality of the classic Swern reaction therefore is retained. Reaction work-up involves brief partitioning of the reaction mixture with water, concentration of the $CH_2Cl_2$ solution, and partitioning of the residue between an apolar solvent (e.g., toluene) and FC72 (a commercial fluorous hydrocarbon). The aldehyde or ketone product is recovered from the apolar solvent phase, while treatment of the FC72 phase with hydrogen peroxide oxidizes the fluorous sulfide to regenerate fluorous DMSO for reuse in the oxidation of an alcohol.

Perfluorohydrocarbons (hereafter termed "fluorinated hydrocarbons"), like FC72, are produced industrially on a large scale. They are immiscible in both common organic solvents and water. Organic chemical substances (e.g., reagents, products, or catalysts) linked to a perfluorohydrocarbon chain (i.e., a fluorinated group) of sufficient chain length are extracted from an organic solvent into a fluorinated hydrocarbon, thereby allowing their facile recovery and recycling. Fluorinated compounds also can be separated from standard organic compounds by preferential retention on a fluorous silica gel followed by a subsequent elution with a fluorinated hydrocarbon.

Oxidations using a fluorous sulfoxide of structural formula (I) also can be activated by other reagents, such as a pyridine-sulfur trioxide complex, acetic anhydride, and carbodiimides, all of which are known activators in variants on the standard Swern oxidation. The present invention also is directed to oxidations using the combination of 3,3,4,4,5,5,6,6,6-nonafluorohexyl methyl sulfide (hereafter termed "fluorous DMS") and its higher and lower homologs, with N-chlorosuccinimide.

The following reaction scheme illustrates the synthesis of fluorous DMS and fluorous DMSO:

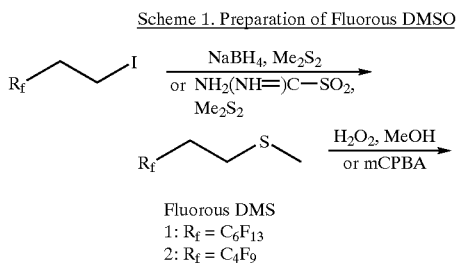

Scheme 1. Preparation of Fluorous DMSO

Fluorous DMS
1: $R_f = C_6F_{13}$
2: $R_f = C_4F_9$

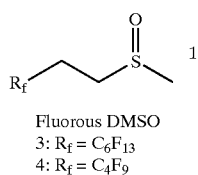

Fluorous DMSO
3: $R_f = C_6F_{13}$
4: $R_f = C_4F_9$

In the above scheme, reduction of dimethyl disulfide with sodium borohydride in ethanol, followed by treatment with commercial 2-perfluoro-hexylethyl iodide provided, after stirring overnight and standard work up, the fluorous sulfide 1 in 74% yield. Alternatively, dimethyl disulfide was reduced with thiourea dioxide in the presence of the fluorous alkyl iodide, and sulfide 1 was obtained in 85% yield. These direct syntheses of sulfide 1 are considerable improvements over an earlier multistep protocol, involving reaction of the iodide with sodium thiocyanate, reduction, and methylation.

Oxidation of fluorous sulfide 1 with hydrogen peroxide in methanol provided fluorous sulfoxide 3 in high overall yield with no overoxidation to the sulfone because more forcing conditions are required for the exhaustive oxidation of sulfide 1. Oxidation with mCPBA (meta-chloroperoxybenzoic acid) also was efficacious, stopping cleanly at the sulfoxide stage, and resulting in a 95% isolated yield of fluorous sulfoxide 3. Sulfoxide 3 is crystalline, white, and odorless, but insoluble in $CH_2Cl_2$ below about $-30°$ C. Therefore, the lower homologous fluorous sulfide 2 and its sulfoxide 4 were prepared in the analogous manner in 71% overall yield from commercial perfluorobutyl-ethyl iodide (Scheme 1). Sulfoxide 4 also is crystalline, white, and odorless, and is soluble in $CH_2Cl_2$ at a temperature as low as $-45°$ C. Sulfoxide 4 has a fluorine content of 55.1% and is recoverable by continuous extraction using a fluorinated solvent (preferred method), or by chromatography over fluorous silica gel. The intermediate fluorous sulfide 3 is relatively volatile, and typically is converted without isolation to sulfoxide 4.

A series of oxidations were conducted wherein fluorous sulfoxide 4 was activated with oxalyl chloride in $CH_2Cl_2$ at $-30°$ C., subsequently treated with an alcohol substrate, then diisopropylethylamine, essentially as in a standard Swern oxidation. Reaction work-up involved brief partitioning of the reaction mixture with water, concentration of the $CH_2Cl_2$ solution, and partitioning of the residue between toluene and FC72 in a continuous extractor for about four hours. The oxidized product (i.e., aldehyde or ketone) then was recovered from the toluene phase, while treatment of the FC72 phase with hydrogen peroxide regenerated sulfoxide 4 for reuse. The results of these oxidations, together with the yields of recovered sulfoxide, are summarized in Table 1.

The following scheme illustrates an oxidation utilizing fluorous DMSO.

Scheme 2. Oxidation with Fluorous DMSO

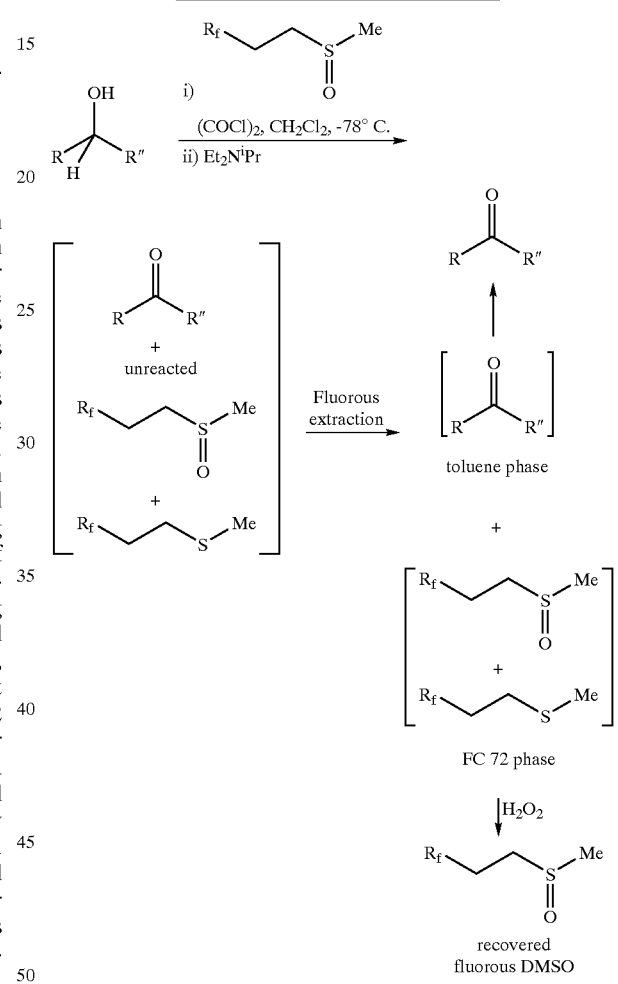

wherein R is a substituted or unsubstituted alkyl or aryl group, and R" is a hydrogen atom or a substituted or unsubstituted alkyl or aryl group.

TABLE 1

Fluorous Swern oxidations

| Example | Alcohol Substrate | Product | % Yield[2] | % Recovered[3] |
|---|---|---|---|---|
| 1 | PhCH₂CH₂CH₂OH | PhCH₂CH₂CHO | 92 | 87 |

TABLE 1-continued

Fluorous Swern oxidations

| Example | Alcohol Substrate | Product | % Yield[2] | % Recovered[3] |
|---|---|---|---|---|
| 2 | allyl-N(Tsoc)-CH2CH2CH2-OH | allyl-N(Tsoc)-CH2CH2-CHO | 77 | 84 |
| 3 | CH2=C(Br)-CH(OTBDMS)-CH2CH2-OH | CH2=C(Br)-CH(OTBDMS)-CH2-CHO | 91 | 88 |
| 4 | 2-nitrobenzyl alcohol | 2-nitrobenzaldehyde | 91 | 86 |
| 5 | phenanthridine-tetrahydro-ol | phenanthridine-dihydro-one | 90 | 89 |
| 6 | borneol | camphor | 94 | 90 |
| 7 | diacetone-protected sugar alcohol | diacetone-protected sugar ketone | 83 | 86 |
| 8 | BnO/OBn protected bicyclic alcohol | BnO/OBn protected bicyclic ketone | 81 | 86 |
| 9[1] | β-lactam hydroxyethyl OBu ester, N-DAM | β-lactam acetyl OBu ester, N-DAM | 81 | 84 |
| 10 | 3-methoxy-estra-1,3,5(10),15-tetraen-17-ol | 3-methoxy-estra-1,3,5(10),15-tetraen-17-one | 80 | 88 |

TABLE 1-continued

Fluorous Swern oxidations

| Example | Alcohol Substrate | Product | % Yield[2] | % Recovered[3] |
|---|---|---|---|---|
| 11 |  | 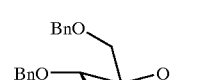 | 79 | 85 |
| 12 | 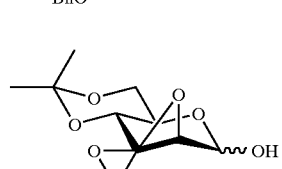 | 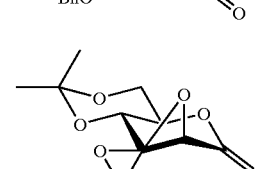 | 86 | 87 |

[1]DAM = dianisylmethyl;
[2]% yield of aldehyde or ketone product; and
[3]% recovery of fluorous DMSO.
[4]Abbreviations:
Tsoc = tri-isopropylsiloxycarbonyl
Bn = benzyl
Bu = butyl
Me = methyl.

An important feature of the present invention is the exchange of dichloromethane ($CH_2Cl_2$) the reaction solvent, for an apolar solvent, like toluene, before the fluorous extraction. At this stage, a majority of sulfoxide 4 has been reduced to sulfide 2, which is very nonpolar and readily recovered in the extraction protocol. However, any residual sulfoxide 4 is not readily extracted from dichloromethane solution, which is attributed to its somewhat polar nature. Replacing dichloromethane by the apolar solvent reduces the affinity of sulfoxide 4 for the organic phase and provides the efficient recoveries of fluorous DMSO summarized in Table 1.

As illustrated in Table 1, the fluorous Swern reaction retains the mild conditions and applicability of the classic Swern reaction in the presence of a wide range of functional groups. The characteristics that contribute to the popularity of the classic Swern reaction, therefore, have been retained. In addition to the typical oxidations of primary and secondary alcohols, Example 2 shows fluorous Swern reaction compatibility with Lipshutz's triisopropylsiloxycarbonyl protecting group (J. Org. Chem., 64, p. 3792 (1999)), the absence of β-elimination of a tert-butyldimethyl-siloxy group (Example 3), and the oxidation of lactols to lactones without β-elimination (Examples 11 and 12).

The mechanism of the fluorous Swern reaction was investigated through the oxidation of monodeuterioisoborneol. In this experiment, camphor was reduced with lithium aluminum deuteride to provide deuterioisoborneol, which then was subjected to oxidation with fluorous sulfoxide 3 in the normal manner. The reaction mixture was subjected to a standard aqueous work-up and fluorous sulfide 1 was recovered by silica gel chromatography. Examination of recovered fluorous sulfide 1 by $^1H$ NMR spectroscopy revealed a diminution in the intensity of the S-methylene group, as well as a change in the coupling pattern of the $R_f$-methylene group, consistent with the incorporation of a deuterium atom into the S-methylene group. This was confirmed by the $^2H$ NMR spectrum of recovered sulfide 1, which exhibited a unique signal at δ 2.86. The reactions, therefore, fall into the category of true Swern oxidations and proceed via a sulfur ylide with subsequent intramolecular hydrogen transfer (Scheme 2). See K. Torssell, Tetrahedron Letters, p. 4445 (1966) and C. R. Johnson et al., J. Org. Chem., 94, p. 3792 (1967). The highly regioselective deprotonation, from the S-methylene rather than the S-methyl group, illustrates the strong electron-withdrawing nature of the fluorous chain and its effect on acidity of neighboring C—H bonds.

Scheme 2. Incorporation of deuterium from deuterioisoborneol into sulfide 1

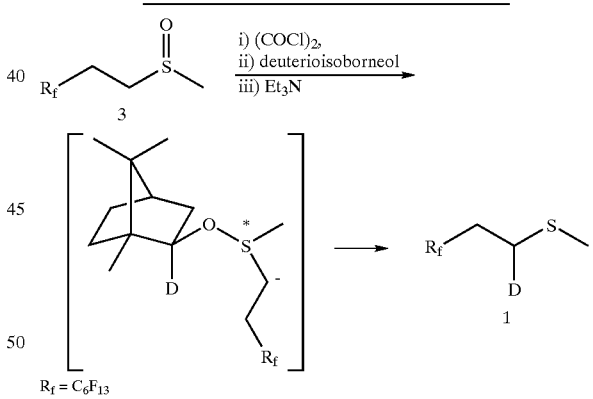

In addition to the fluorous Swern oxidation, a fluorous sulfide having a structure $R_f$—$(CH_2)_n$—S—R, wherein $R_f$, R, and n are as defined above, can be used in a fluorous version of the Corey-Kim reaction (E. J. Corey et al., J. Am. Chem. Soc., 94, p. 7586 (1972)). This reaction uses a fluorous sulfide as opposed to a fluorous sulfoxide and, therefore, it is preferable to use a less volatile higher sulfide homolog (e.g., sulfide 1). Several examples of the use of a fluorous sulfide in a Corey-Kim reaction are illustrated in Table 2. In order to obtain a high recovery of the fluorous sulfide, it was necessary to use as near stoichiometric sulfide as possible. This is because excess sulfide is oxidized by the excess N-chlorosuccinamide and is not recoverable in the form of the sulfide.

TABLE 2

Fluorous Corey - Kim oxidations

| Example | Substrate | Product | % Yield | % Recovery |
|---|---|---|---|---|
| 13 | 3-phenylpropan-1-ol | 3-phenylpropanal | 83 | 76 |
| 14 | 2-nitrobenzyl alcohol | 2-nitrobenzaldehyde | 86 | 73 |
| 15 | hydroxy-tetrahydrophenanthridine | oxo-tetrahydrophenanthridine | 78 | 73 |
| 16 | borneol | camphor | 88 | 72 |
| 17 | octan-1-ol | octanal | 88 | 75 |

An important feature of the present invention is recovery of the fluorous sulfide in a high yield by extraction with a fluorinated solvent, followed by oxidation with hydrogen peroxide to regenerate fluorous sulfoxide (I). Another important feature of the present invention is to substitute an apolar solvent for the chlorinated solvent used in the reaction, prior to the extraction step.

An apolar solvent useful in the extraction is insoluble in a fluorinated solvent and has a high solvency for the reaction product. Examples of aprotic solvents include, but are not limited to, toluene, benzene, xylene, ethylbenzene, mesitylene, hexane, heptane, pentane, petroleum ether, light petroleum, ligroin, and other nonpolar aromatic and aliphatic hydrocarbon solvents, and mixtures thereof.

Fluorinated solvents useful in the extraction of the fluorous sulfide include, but are not limited to, aliphatic perfluorocarbons containing five to ten carbon atoms and perfluorinated cycloalkanes containing six to ten carbon atoms. Specific examples of fluorinated solvents include, but are not limited to, perfluorohexane, perfluoroheptane, perfluorooctane, perfluorononane, perfluorocyclohexane, perfluoromethylcyclohexane, perfluoro-1,2-dimethylcyclohexane, perfluoro-1,3-dimethylcyclohexane, cis-perfluorodecalin, trans-perfluorodecalin, perfluorokerosene, perfluoromethyldecalin, FC-72, and mixtures thereof.

After recovery of the fluorous sulfide and oxidation of the sulfide to a fluorous sulfoxide (I), the recycled fluorous sulfoxide (I) performed analogously to freshly synthesized fluorous sulfoxide (I). In fact, fluorous sulfoxide (I) was routinely recovered and recycled with no attempt to discriminate from virgin material.

The following examples illustrate an efficient method of preparing and using a fluorous sulfoxide (I) in a Swern reaction. A wide range of primary and secondary alcohols can be oxidized to the corresponding aldehydes and ketones, in high yield, and under completely odor-free reactions. The fluorous sulfoxide (I) then is recovered for reuse by a simple continuous fluorous extraction and reoxidation using hydrogen peroxide.

EXPERIMENTAL PROCEDURES

General

All reagents were purchased from commercial sources and used as received, unless otherwise indicated. Tetrahydrofuran and benzene were distilled from sodium/benzophenone ketyl, and methylene chloride was distilled from calcium hydride prior to use. $^1H$, $^2H$, $^{13}C$, and $^{19}F$ NMR spectra were recorded in deuteriochloroform solutions at 500 or 300, 77, 125 or 75, and 282 MHz, respectively. Elemental analyses were performed by Midwest Microlabs, Indianapolis, Ind. All reactions were performed under a dry argon atmosphere unless otherwise stated. With the exception of the substrate used in Example 2, oxidation substrates were either commercially available or prepared as described in the literature. With the exception of the product of Example 2, oxidation products were identical to either commercial or literature samples.

Method of Preparing Fluorous Sulfides and Sulfoxides by Borohydride Reduction of Dimethyl Disulfide and Hydrogen Peroxide Oxidation Sodium borohydride ($NaBH_4$) (1.4 g, 37.0 mmol) was added under an argon atmosphere to a stirred solution of dimethyl disulfide ($Me_2S_2$) (3.3 g, 35.0 mmol) in ethanol (EtOH) (25 mL). After stirring for 30 minutes, the reaction mixture was cooled to 0° C., then a solution of 6,6,6,5,5,4,4,3,3-nonafluorohexyl iodide (perfluorobutylethyl iodide) (10 g, 26.7 mmol) in anhydrous THF (15 mL) was added drop-wise over a period of 1 hour. The reaction mixture then was stirred overnight at room temperature before additional dimethyl disulfide (1.0 g, 10.6 mmol) reduced with sodium borohydride (0.45 g, 11.9 mmol) in ethanol (10 mL) was added. After stirring for an additional 6 hours, the reaction mixture was diluted with hexanes (20 mL) and washed with water and brine. The hexane layer was diluted with methanol (10 mL) and hydrogen peroxide (3.1 mL of 30%, 27 mmol), then stirred at room temperature for 1 hour. The reaction mixture next was diluted with dichloromethane (25 mL), washed with water, dried over sodium sulfate ($Na_2SO_4$), and concentrated in vacuo to give fluorous DMSO (compound 4) (5.9 g, 19.0 mmol, 71%) as a crystalline white solid (m.p. 46° C.)

Method of Forming Fluorous Sulfides by Thiourea Sulfur Dioxide Reduction of Dimethyl Disulfide To a mixture of perfluorohexylethyl iodide (1.0 g, 2 mmol), $Me_2S_2$ (0.094 g, 1 mmol), thiourea dioxide ($NH_2$($NH=$)$C—SO_2$) (0.11 g, 1 mmol), and cetyltrimethylammonium bromide (20 mg, 0.05 mmol) in THF (8 mL) under argon was added 6% aqueous sodium hydroxide (NaOH) (8 mL), followed by heating to reflux for 4 to 5 hours. After cooling to room temperature, the organic layer was separated, and the aqueous layer washed with ethyl acetate. Concentration of the extracts and flash chromatography on silica gel eluting with hexanes yielded pure fluorous sulfide 1 (0.67 g, 85%).

Method of Oxidizing Fluorous Sulfides to Sulfoxides With mCPBA

To fluorous sulfide 1 (0.25 g, 0.6 mmol) dissolved in $CH_2Cl_2$ (5 mL) at −78° C. was added metachloroperoxybenzoic acid (mCPBA) (0.14 g, 77%, 0.6 mmol) portionwise. The reaction mixture was allowed to warm to 0° C., then stirred for an additional 10 minutes before quenching by addition of saturated aqueous sodium bicarbonate ($NaHCO_3$). The organic layer was washed further with water and brine, and the solvents evaporated to give pure crystalline fluorous sulfoxide 3 (0.25 g, 95%).

1,1,1,2,2,3,3,4,4,5,5,6,6-Tridecafluoro-8-methanesulfenyloctane (Compound 1)

$^1$H NMR: δ 2.76–2.73 (m, 2H); 2.47–2.36 (m, 2H); 2.18 (s, 3H); $^{13}$C NMR: δ 119.9–108.7 (m), 32.3 (5), 25.1 (s), 15.9 (s); $^{19}$F NMR: δ−53.8, −51.0 (d), −50.5, −49.5, −42.0 (m), −8.5 (t). Anal. calcd for $C_9H_7F_{13}S$: C, 27.42, H, 1.79; Found: C, 27.45, H, 1.72.

1,1,1,2,2,3,3,4,4-Nonafluoro-6-methanesulfenylhexane (Compound 2)

$^1$H NMR: δ 2.76–2.73 (m, 2H); 2.47–2.36 (m, 2H); 2.18 (s, 3H); $^{13}$C NMR: δ 117.1–108.2 (m), 32.1 (t), 25.0 (s), 15.9 (s); $^{19}$F NMR: δ −53.7 (t), −52.0 (d), −42.2 (t), −8.7 (t). See S. Dieng et al., *J. Fluorine Chem.*, 28, p. 425 (1985).

1,1,1,2,2,3,3,4,4,5,5,6,6-Tridecafluoro-8-methanesulfinyloctane (Compound 3)

Mp 64° C.; $^1$H NMR: δ 3.04–2.98 (m, 1H); 2.92–2.86 (m, 1H); 2.72–2.61 (m, including a s at 2.68, 5H); $^{13}$C NMR: δ 133.3–128.4 (m), 118.8–111.1 (m), 45.1 (s), 39.3 (s), 25.1 (t); $^{19}$F NMR: δ−8.4 (d), −41.1, −49.4, −50.5, −50.8, −53.7 (d). Anal. calcd for $C_9H_7F_{13}SO$: C, 26.35, H, 1.72; Found: C, 26.29, H. 1.71.

1,1,1,2,2,3,3,4,4-Nonafluoro-6-methanesulfinylhexane (Compound 4)

Mp 46° C.; $^1$H NMR: δ 3.04–2.98 (m, 1H); 2.92–2.86 (m, 1H); 2.72–2.61 (m, including a s at 2.68, 5H); $^{13}$C NMR: δ 133.3–128.4 (m), 118.8–108.6 (m), 45.1 (s), 39.3 (s), 25.0 (t); $^{19}$F NMR: δ−8.5 (t), −41.3 (m), −51.7 (d), −53.6 (t). Anal. calcd for $C_7H_7F_9SO$: C, 27.11, H, 2.27; Found: C, 27.44, H. 2.44.

O-Triisopropylsilyl N-allyl-N-4-hydroxybutyl)-carbamate (Alcohol Substrate of Example 2)

To a solution of 4-allylaminobutan-l-ol (D. Crich et al., *Org. Lett.*, 3, p. 1917 (2001)) (1.06 g. 8.27 mmol) in $CH_2Cl_2$ (30 mL) was added triethylamine ($Et_3N$) (5.6 mL, 20.6 mmol) followed by cooling to −78° C. and the bubbling of dry carbon dioxide ($CO_2$) for 2.5 hours. Tri-isopropylsilyl trifluoromethanesulfonate (TIPSOTf) (2.6 mL, 9.9 mmol) then was added dropwise at −78° C. and stirring continued at −78° C. for 1.5 hours before the solution was gradually warmed to room temperature and stirred for 2 hours. The reaction mixture then was diluted with water (50 mL) and the aqueous layer extracted with $CH_2Cl_2$ (3×70 mL). The combined organic layers were washed with saturated aqueous $NaHCO_3$ (3×50 mL), water (2×50 mL), and brine (2×50 mL), dried ($Na_2SO_4$), and concentrated under reduced pressure. Purification by column chromatography on silica gel (hexanes/ethyl acetate 3:1) gave the title compound (2.53 g, 93%) as a colorless oil. $^1$H NMR (50° C.) δ 5.83–5.73 (m, 1H), 5.16–5.09 (m, 2H), 3.86 (d, J=5.7 Hz, 2H), 3.63 (t, J=6 Hz, 2H), 3.26 (t, J=7.5 Hz, 2H), 1.68–1.48 (m, 4H), 1.36–1.23 (m, J=7.2 Hz, 3H), 1.08 (d, J=7.2 Hz, 18H); $^{13}$C NMR δ 155.1, 134.2, 116.2, 62.5, 50.3, 49.7, 47.3, 46.7, 30.1, 29.8, 25.1, 24.5, 17.9, 17.5, 12.7, 12.2. Anal. calcd for $C_{17}H_{35}NO_3Si$: C, 61.96; H, 10.70. Found: C, 62.20; H, 10.82.

O-Triisopropylsilyl N-allyl-N-(4-oxobutyl) carbamate (Product of Example 2)

$^1$H NMR δ 9.68 (t, J=1.3 Hz, 1H), 5.78–5.61 (m, 1H), 5.03 (br, d, J=12 Hz, 2H), 3.74 (br, s, 2H), 3.13 (t, J=6.3 Hz, 2H), 2.37 (t, J=7.2 Hz, 2H), 1.75 (quintet, J=7.2 Hz, 2H), 1.36 (s, 9H); $^{13}$C NMR δ 201.8, 155.2, 134.1, 116.6, 116.4, 116.3, 79.7, 49.8, 49.3, 45.7, 45.6, 41.1, 28.5, 23.6, 20.8. Anal. calcd for $C_{17}H_{33}NO_3Si$; C, 63.41; H, 9.31, Found: C, 63.16; H, 9.19.

General Method of Oxidizing Alcohols and Recovery of a Fluorous Sulfoxide

To a well-stirred solution of anhydrous $CH_2Cl_2$ (5 mL) under an argon atmosphere at −30° C. was added oxalyl chloride (0.14 mL, 1.6 mmol). Fluorous DMSO (1.0 g, 3.2 mmol) then was added dropwise, and the reaction mixture stirred for an additional 20 minutes. Isoborneol (0.153 g, 1 mmol) dissolved in $CH_2Cl_2$ (5 mL) then was added to this solution, followed, after an additional 40 min to 1 hour, by diisopropylethylamine (0.88 mL, 5 mmol). The reaction mixture then was warmed to room temperature and stirred for 30 minutes before quenching with water, washing with ammonium chloride (5 mL), extracting with $CH_2Cl_2$ (10 mL), and careful concentration under aspirator vacuum in a cold water bath. The reaction mixture then was dissolved in toluene (6 mL) and extracted continuously, with FC72 (15 mL) in a cooled continuous extractor for 4 hours (see, D. Crich et al., "Design, Synthesis, Application and Recovery of a Minimally Fluorous Diaryl Diselenide for the Catalysis of Stannane-Mediated Radical Chain Reactions," *Tetrahedron*, 55, pp. 14261–14268 (1999)). After decantation, concentration of the toluene layer and chromatography on silica gel yielded camphor (0.142 g, 94%). The FC72 phase, containing a mixture of fluorous. DMS and fluorous DMSO, then was stirred with methanol (3 mL) and hydrogen peroxide (0.23 mL of 30 %, 2 mmol) for 1 hour followed by dilution with water (5 mL), and extraction with $CH_2Cl_2$ (10 mL) in a three phase system. Concentration of the $CH_2Cl_2$ layer gave recovered crystalline fluorous DMSO (0.9 g, 90%).

2-Deuterioisoborneol

To a slurry of lithium aluminum deuteride ($LiAlD_4$) (0.012 g) in anhydrous ether (1 mL) was added, with stirring, camphor (0.1 g) in ether (2 mL), followed by heating at reflux for 3 hours. After cooling to room temperature, the excess hydride was decomposed by addition of moist ether, then the organic layer was washed with brine, dried ($Na_2CO_4$) and evaporated to give a quantitative yield of deuteriated isoborneol (0.1 g). $^2H$ NMR (hexanes): δ 3.75. See B. Belleau, *J. Am. Chem. Soc.*, 82, p. 5751 (1960).

Fluorous Oxidation of Deuterioisoborneol

The fluorous oxidation was performed using fluorous sulfoxide 3 by the standard protocol with the exception of the work-up and isolation. When the oxidation was complete (TLC), the reaction was quenched with saturated aqueous ammonium chloride ($NH_4Cl$), and the organic layer carefully concentrated. The residue then was deposited on a short silica gel column, which was eluted with hexanes. Evaporation of the eluent gave the deuteriated fluorous sulfide 1. $^2H$ NMR (hexanes): δ 2.86.

General Procedure for the Corey-Kim Oxidation Using a Fluorous Sulfide (Compound 1)

To a solution of N-chlorosuccinimide (0.1 g, 0.8 mmol) in toluene (2 mL) was added flurous sulfide 1 (0.4 g, 1 mmol) at 0° C. resulting in the immediate formation of a white cloudy precipitate. The reaction mixture was cooled to −25° C., and a solution of octanol (0.07 g, 0.5 mmol) in toluene (2 mL) was added. After stirring at −25° C. for 2 hours, a solution of $Et_3N$ (0.08 g, 0.8 mmol) was added. The cold bath was removed after 5 minutes, and the reaction mixture washed with saturated aqueous $NH_4Cl$, then water. The organic layer was extracted continuously with FC72 solvent (15 mL) in a cooled continuous extractor for a period of 4 hours. Concentration of the toluene layer and chromatography on silica gel (eluent: EtOAc/hexanes 3:1) yielded octanal (0.06 g, 88%). The FC72 layer was carefully concentrated under aspirator vacuum to give recovered fluorous sulfide 1 (0.3 g, 75%).

The present invention, therefore, is directed to efficient methods of preparing fluorous sulfides and their oxidation to the corresponding fluorous sulfoxides. The fluorous sulfoxides in conjunction with oxalyl chloride and Hunig's base, oxidize diversely functionalized primary and secondary alcohols to aldehydes and ketones in excellent yield. The fluorous sulfoxide is efficiently recovered for reuse by a simple continuous fluorous extraction of the sulfide, followed by hydrogen peroxide oxidation. The entire oxidation process is odor free and suitable for industrial scale oxidations. A deuterium-labeling experiment demonstrated that the oxidations via the classical Swern mechanism. Corey-Kim oxidations also can be performed using the fluorous sulfides.

Obviously, many modifications and variations of the invention as hereinbefore set forth can be made without departing from the spirit and scope thereof, and, therefore, only such limitations should be imposed as are indicated by the appended claims.

What is claimed is:

1. A fluorous sulfoxide having a structure

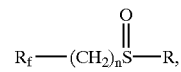

wherein $R_f$ is a fluorinated hydrocarbon chain containing one to twelve carbon atoms; R is $C_{1-4}$alkyl or $(CH_2)_n$—$R_f$; and n is 1 to 3, wherein the sulfoxide contains at least 35%, by weight, fluorine.

2. The sulfoxide of claim 1 wherein $R_f$ contains four to ten carbon atoms.

3. The sulfoxide of claim 1 wherein $R_f$ contains six to eight carbon atoms.

4. The sulfoxide of claim 1 wherein $R_f$ is perfluorinated.

5. The sulfoxide of claim 1 containing at least 35% to about 65%, by weight, fluorine.

6. The sulfoxide of claim 1 wherein R is methyl or ethyl.

7. The sulfoxide of claim 1 wherein n is 2.

8. The sulfoxide of claim 1 wherein $R_f$ is $C_6F_{13}$ or $C_4F_9$.

9. The sulfoxide of claim 1 wherein the sulfoxide is

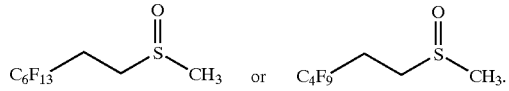

10. A method of oxidizing a primary or secondary alcohol to an aldehyde or ketone comprising reacting the alcohol with a fluorous sulfoxide having a structure

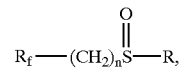

wherein $R_f$ is a fluorinated hydrocarbon chain containing one to twelve carbon atoms; R is $C_{1-4}$alkyl or $(CH_2)_n$—$R_f$; and n is 1 to 3, in the presence of an activator, followed by treatment with an organic base.

11. The method of claim 10 wherein $R_f$ is perfluorinated.

12. The method of claim 10 wherein $R_f$ is $C_4F_9$ or $C_6H_{13}$.

13. The method of claim 10 wherein the fluorous sulfoxide is

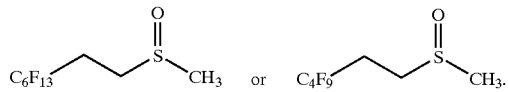

14. The method of claim 10 wherein the activator is selected from the group consisting of oxalyl chloride, pyridine-sulfur trioxide complex, acetic anhydride, a carbodiimide; and N-chloro-succinamide.

15. The method of claim 10 wherein the base is diisopropylethylamine.

16. The method of claim 10 comprising further steps wherein a sulfide by-product of the oxidation reaction having a formula $R_f\text{---}(CH_2)_n\text{---}S\text{---}R$ is separated from the reaction mixture, then oxidized using an oxidizing agent to regenerate

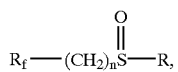

17. The method of claim 16 wherein the oxidizing agent is hydrogen peroxide.

18. The method of claim 16 wherein the sulfide by-product is separated from the reaction mixture by extraction using a fluorinated solvent.

19. The method of claim 18 wherein the fluorinated solvent is selected from the group consisting of perfluorohexane, perfluoroheptane, perfluorooctane, perfluorononane, perfluorocyclohexane, perfluoromethylcyclohexane, perfluoro-1, 2-dimethylcyclohexane, perfluoro-1, 3-dimethylcyclohexane, cis-perfluorodecalin, trans-perfluorodecalin, perfluorokerosene, perfluoromethyldecalin, and mixtures thereof.

* * * * *